United States Patent
Hettrick et al.

(10) Patent No.: US 7,792,581 B2
(45) Date of Patent: Sep. 7, 2010

(54) METHOD AND APPARATUS FOR TREATING DIASTOLIC HEART FAILURE

(75) Inventors: Douglas A. Hettrick, Blaine, MN (US); Lawrence J. Mulligan, Andover, MN (US); David E. Euler, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 689 days.

(21) Appl. No.: 11/363,729

(22) Filed: Feb. 28, 2006

(65) Prior Publication Data
US 2007/0203522 A1    Aug. 30, 2007

(51) Int. Cl.
*A61N 1/365* (2006.01)
(52) U.S. Cl. .......................... 607/19; 607/18
(58) Field of Classification Search ............ 607/9, 607/17–19
See application file for complete search history.

(56) References Cited

U.S. PATENT DOCUMENTS

| 5,154,170 | A | * | 10/1992 | Bennett et al. | 607/17 |
|---|---|---|---|---|---|
| 5,176,137 | A | * | 1/1993 | Erickson et al. | 607/4 |
| 5,334,221 | A | | 8/1994 | Hettrick | |
| 5,356,425 | A | | 10/1994 | Bardy et al. | |
| 6,006,134 | A | | 12/1999 | Hill et al. | |
| 6,073,048 | A | | 6/2000 | Kieval et al. | |
| 6,606,517 | B1 | | 8/2003 | Park et al. | |
| 6,622,041 | B2 | | 9/2003 | Terry et al. | |
| 6,887,207 | B2 | | 5/2005 | Hettrick | |
| 6,941,170 | B1 | | 9/2005 | Lu | |
| 7,027,863 | B1 | | 4/2006 | Prutchi et al. | |
| 7,269,457 | B2 | | 9/2007 | Shafer et al. | |
| 7,305,265 | B2 | | 12/2007 | Fukui | |
| 7,416,529 | B2 | * | 8/2008 | Hedberg | 600/485 |
| 7,460,907 | B1 | | 12/2008 | Darvish et al. | |
| 2002/0091332 | A1 | * | 7/2002 | Bombardini | 600/510 |
| 2002/0120305 | A1 | * | 8/2002 | Sun et al. | 607/19 |
| 2002/0136691 | A1 | * | 9/2002 | Harrison et al. | 424/9.2 |
| 2004/0167410 | A1 | * | 8/2004 | Hettrick | 600/486 |
| 2004/0220637 | A1 | * | 11/2004 | Zdeblick et al. | 607/17 |
| 2005/0075675 | A1 | * | 4/2005 | Mulligan et al. | 607/9 |

FOREIGN PATENT DOCUMENTS

WO    WO0126729 A    4/2001

OTHER PUBLICATIONS

Torosoff et al. "Improving Outcomes in Diastolic Heart Failure Techniques to Evaluate Underlying Causes and Target Therapy" http://www.postgradmed.com/issues/2003/03_03/torosoff2.htm vol. 113 / No. 3 / Mar. 2003 / Postgraduate Medicine.

(Continued)

*Primary Examiner*—George R Evanisko
(74) *Attorney, Agent, or Firm*—Stephen W. Bauer

(57) ABSTRACT

Methods and systems for treating patients with diastolic heart failure (DHF) are disclosed which include slowing a patient's heart rate below its intrinsic rate, and controlling the rate using cardiac pacing therapy to improve LV filling and cardiac output. In certain embodiments, a pacing treatment rate may be determined by adjusting an adaptive rate by an amount determined by evaluating one or more patient parameters.

7 Claims, 10 Drawing Sheets

OTHER PUBLICATIONS

Maurer, MS et al. Diastolic Dysfunction: Can it be diagnosed by doppler echocardiography? J Am Coll Cardiol 2004; 44: 1543-9.

Vasan et al. Prevalence, clinical features and prognosis of diastolic heart failure: an epidemiologic perspective. J Am Coll Cardiol 1995; 26(7): 1565-74.

Zile et al., Contractile behavior of the left ventricle in diastolic heart failure: with emphasis on regional systolic function. Circulation 2006: 113:296-304.

Shinke et al. Beneficial effects of heart rate reduction on cardiac mechanics and energetics in patients with left ventricular dysfunction. Jpn Circ J 1999; 63:957-964.

Bleasdale et al., Left ventricular pacing minimizes diastolic ventricular interaction, allowing improved preload-dependent systolic performance. Circulation. 2004; 110:2395-2400.

Pepine et al. Aortic input impedance during nitroprusside infusion: a reconsideration of afterload reduction and beneficial action. J. Clin. Invest 1979 64:643-654.

Kass et al., What mechanisms underlie diastolic dysfunction in heart failure? Circ. Res. 2004;94:1533-1542.

Zile et al., New concepts in diastolic dysfunction and diastolic heart failure: Part I; Diagnosis, Prognosis, and Measurements of Diastolic Function. Circulation. 2002; 105: 1387-1393.

Zile et al., New concepts in diastolic dysfunction and diastolic heart failure: Part II; Causal Mechanisms and Treatment. circulation 2002; 105:1503-1508.

Gaasch et al., Left ventricular diastolic dysfunction and diastolic heart failure. Annu. Rev. Med. 2004. 55:373-94.

Zile et al., Diastolic heart failure—abnormalties in active relaxation and passive stiffness of the left ventricle. N Engl J Med 2004; 350:1953-9.

* cited by examiner

METHOD AND APPARATUS FOR TREATING DIASTOLIC HEART FAILURE

FIELD

The present invention relates generally to medical devices, and more particularly to implantable medical devices (IMDs).

BACKGROUND

Diastolic Heart Failure ("DHF"), a major cause of morbidity and mortality, is a clinical phenomena characterized by low cardiac output and/or symptoms of congestion with normal (or above normal) ejection fraction. Clinical diagnosis of DHF may typically also require evidence of reduced left ventricular (LV) filling. This evidence may be obtained from a Doppler echo examination, for example.

DHF may relate to a disease of the myocardium, or may alternately be indicative of other clinical pathologies such as hypertension, myocardial infarction, coronary artery disease, aging, diabetes mellitus, obesity, or aortic stenosis, for example without limitation. Hypertension may be an important co-morbidity of DHF, accounting for about 60% of patients with DHF. DHF may represent more than about 40% of the total congestive heart failure ("CHF") population according to some estimates.

Appropriate clinical treatment for DHF is not as well established as for systolic heart failure ("SHF"), and usually mimics the treatment given for SHF, despite the fact that the underlying disease processes are not necessarily similar. A type of treatment may include pharmacologic treatment, such as calcium channel blockers, diuretics, inotropes, beta-blockers and ACE inhibitors, for example. Some evidence may suggest DHF patients may respond to cardiac resynchronization therapy (CRT), but evidence to support this hypothesis is currently lacking.

DHF patients often have thick, hypertrophic ventricular walls, resulting in increased myocardial "stiffness." Increased sympathetic tone may lead to higher than normal basal heart rates in patients with DHF. However, DHF patients may not benefit from an increase in heart rate, and may experience a worsening of symptoms in some cases, since an increase in rate tends to reduce LV diastolic filling time, and hence, may further reduce LV filling. Increasing HR in a patient with DHF may also reduce coronary perfusion (which may depend on filling time). Symptoms that may arise due to DHF may become more pronounced during exercise, since end diastolic volume in a DHF patient tends to stay the same during exercise, rather than increasing to meet increased demands. Thus, tolerable ranges for heart rate for a patient with DHF may be more difficult to determine than for other individuals.

SUMMARY OF THE INVENTION

In certain embodiments of the invention, apparatus and methods for treating diastolic heart failure (DHF) are disclosed which involve slowing a patient's base heart rate below their intrinsic rate, and controlling the rate using cardiac pacing therapy at a treatment rate to improve cardiac output. The treatment rate may be adjusted or modulated by a rate adjustment parameter, which may be determined by evaluation of one or more monitored patient parameters in accordance with embodiments of the invention.

DETAILED DESCRIPTION

Figure 1:
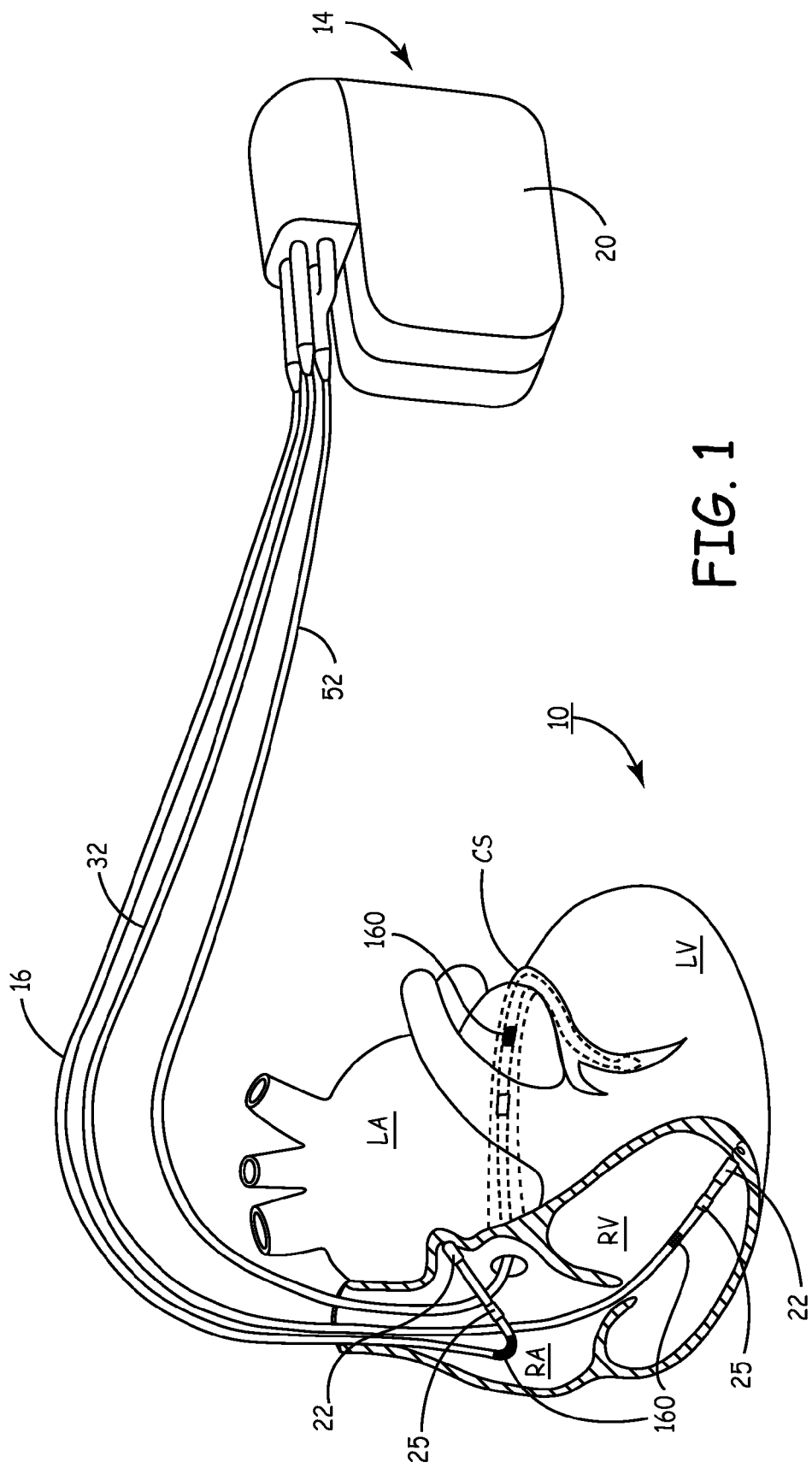
FIG. 1 is a schematic diagram depicting a multi-channel, atrial and bi-ventricular, monitoring/pacing implantable medical device (IMD) in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Diastolic Heart Failure (DHF) is a clinical phenomenon associated with congestive heart failure (CHF) in which left ventricular ejection fraction (LVEF) may be relatively normal (or elevated), and pulmonary congestion may occur due to impaired left ventricular (LV) filling. DHF may evolve from a distinct cardiomyopathy, but may be more commonly associated with other pathologies such as hypertension, myocardial infarction, and coronary artery disease, for example without limitation. DHF may also be associated with LV hypertrophy and impaired coronary perfusion.

In patients with DHF, increases in heart rate may exacerbate symptoms by limiting diastolic filling time and coronary perfusion, since coronary perfusion occurs during diastole. On the other hand, a reduction in heart rate may provide a benefit for patients with DHF. Methods and systems in accordance with certain embodiments of the invention may therefore attempt to modulate heart rate to increase LV filling and coronary perfusion. Certain embodiments of the invention may include, or may be adapted for use in, diagnostic monitoring equipment, external medical device systems, and implantable medical devices (IMDs), including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM).

In FIG. 1, heart 10 includes the right atrium (RA), left atrium (LA), right ventricle (RV), left ventricle (LV), and the coronary sinus (CS) extending from the opening in the right atrium laterally around the atria to form the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
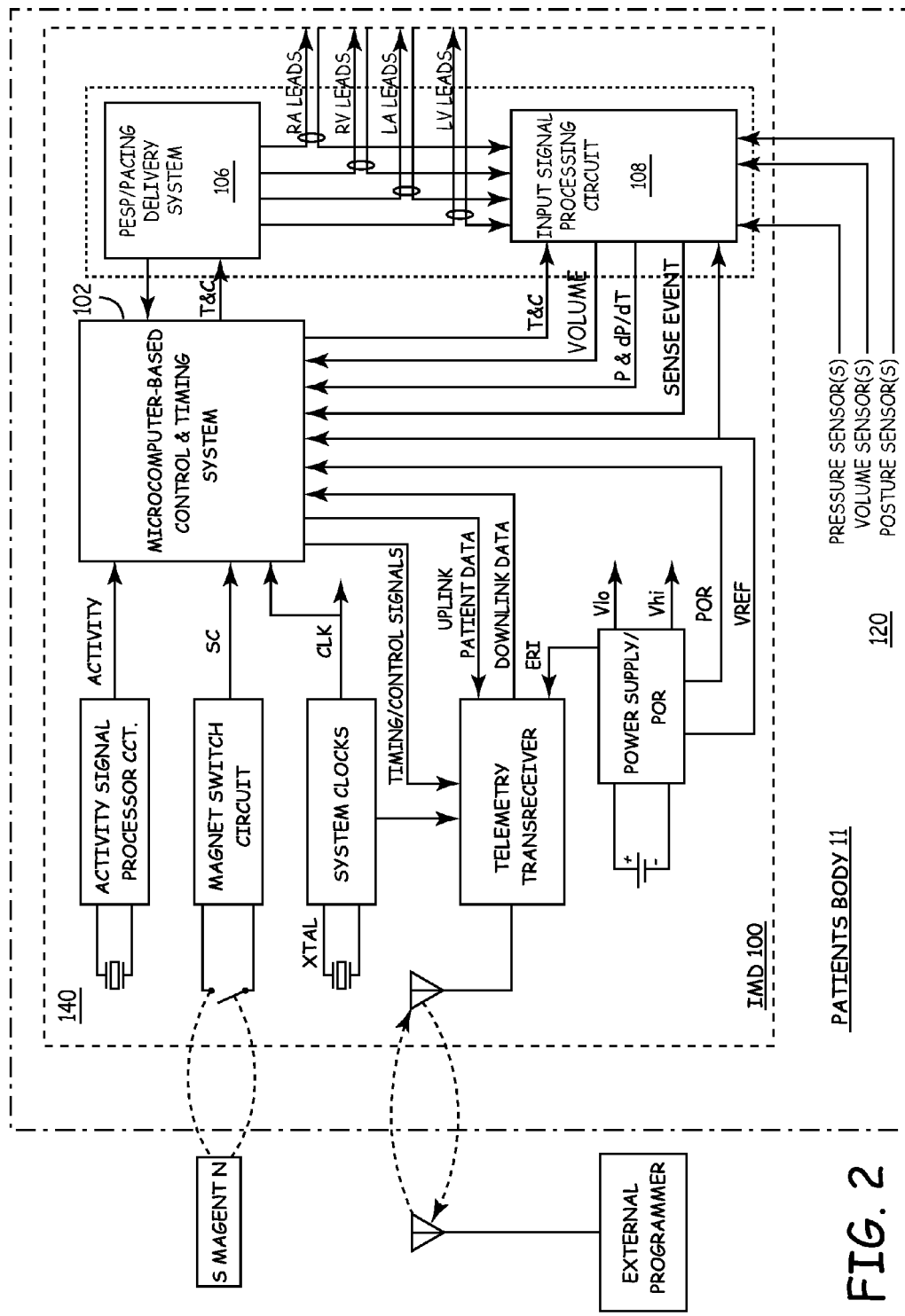
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include other physiologic or hemodynamic sensors.

Figure 3:
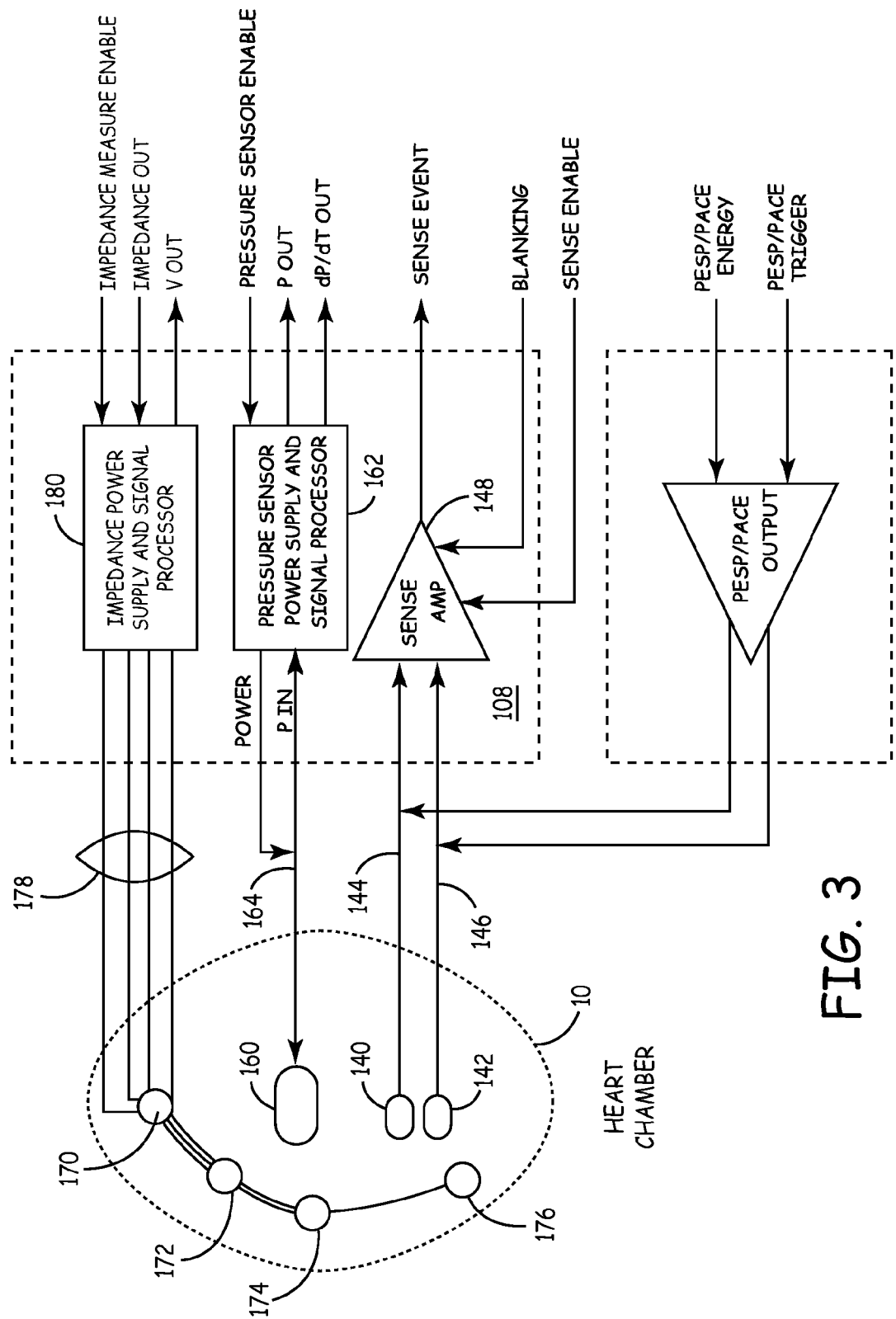
FIG. 3 is a simplified block diagram of a single monitoring and pacing channel for acquiring pressure, impedance and cardiac EGM signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

In patients with DHF, left ventricular ejection fraction (LVEF) may be normal, or even relatively high, but LV filling may be impaired (e.g., low pre-load). Congestive heart failure (CHF) has typically been treated by raising heart rate (HR) to improve cardiac output. However, raising HR in a DHF patient may worsen the situation, since it reduces LV diastolic filling time, and hence, may further reduce LV filling. Increasing HR in a patient with DHF may also reduce coronary perfusion (which may depend on filling time).

In general, patients with DHF may benefit from a reduction in HR to thereby increase LV filling time, according to certain embodiments of the invention. A recent study demonstrated that reducing heart rate via a specific bradycardic agent (e.g., ULFS-49) improved cardiac efficiency in patients with heart failure. By contrast, increasing heart rate temporarily, for example, via atrial pacing, tended to reduce cardiac efficiency.

In certain embodiments, the patient's base HR may be reduced below the intrinsic rate using techniques known to those of ordinary skill in the art. Reducing the base HR below the intrinsic rate may enable the patient's HR to be controlled via cardiac pacing therapy at a therapy rate which may be at, above, or below the intrinsic rate. The base HR may be reduced by ablating certain portions of the electrical conduction system of the heart, such as the sino-atrial (SA) node and/or the atrio-ventricular (AV) node, for example. Pharmacologic therapy may also be employed to reduce the patient's HR, as may certain forms of pacing therapy which employ post extra-systolic potentiation (PESP) to decrease HR.

In certain preferred embodiments of the invention, an SA nodal ablation may be performed to lower the base HR, while maintaining the AV node intact to promote intrinsic conduction into the ventricles. Cardiac pacing may be employed in an atrial-based pacing mode, such as AAI/AAIR, to control and/or modulate HR at a therapy rate. Of course, one of ordinary skill in the art would recognize that other pacing modes, including certain dual-chamber pacing modes, could also be employed to accomplish a similar result. An AV nodal ablation may alternately or additionally be performed to lower the base HR, thereby allowing HR to be controlled or modulated via cardiac pacing at a therapy rate. In certain embodiments, pharmacologic therapy (i.e., drug therapy) may be used either alone or in conjunction with ablative techniques to lower the base HR.

Once a DHF patient's base HR has been lowered to a rate lower than intrinsic, the patient's HR may be controlled by the delivery of cardiac pacing, for example, in the AAI/AAIR mode. The AAI/AAIR pacing modes may be desirable since they tend to preserve intrinsic ventricular conduction (e.g., conduction through the AV node, his bundle, and bundle branches). AAI/AAIR pacing at a rate lower than the patient's intrinsic rate, for example, may improve cardiac function by increasing pre-load, and hence, may improve cardiac output. Coronary perfusion may also be increased due to the longer periods of diastole associated with the lowered pacing rate. In addition to improved coronary perfusion, myocardial oxygen demand may be reduced, thereby improving cardiac efficiency.

The pacing rate (and/or pacing mode and/or other pacing parameters) may be adjusted or modulated, for example, in response to changes in physiologic demand, according to certain embodiments. In an exemplary embodiment of the invention, a method is provided by which an adaptive pacing rate, $R_O$, is first determined based upon an activity sensor and/or a physiological sensor signal, and is then adjusted or modulated based upon other sensor signals to determine a treatment rate, $R_T$. Such an embodiment could employ closed loop control using feedback from an implantable sensor. Implantable sensors that may be used as the basis for adjusting or modulating the adaptive rate, $R_O$, may include, but are not limited to, hemodynamic pressure and flow sensors (e.g., RVP, LVP, ePAD, LAV coronary venous, etc.), oxygen sensors, sonomicrometry, impedance, minute ventilation, accelerometer, dP/dt, etc. For example, hemodynamic pressure sensor signals may be used to measure (or estimate) "LV afterload," and may therefore be used as a feedback mechanism to adjust a certain pacing parameter, such as rate, to reach a target level of LV afterload. LV afterload is a measure of the forces opposing ejection. These forces may be determined in part by the resistive and compliant mechanical properties of the arterial system. Because arterial compliance is a function of frequency, LV afterload can be modulated by varying HR (and hence, frequency).

Figures 4A, 4B, 4C:
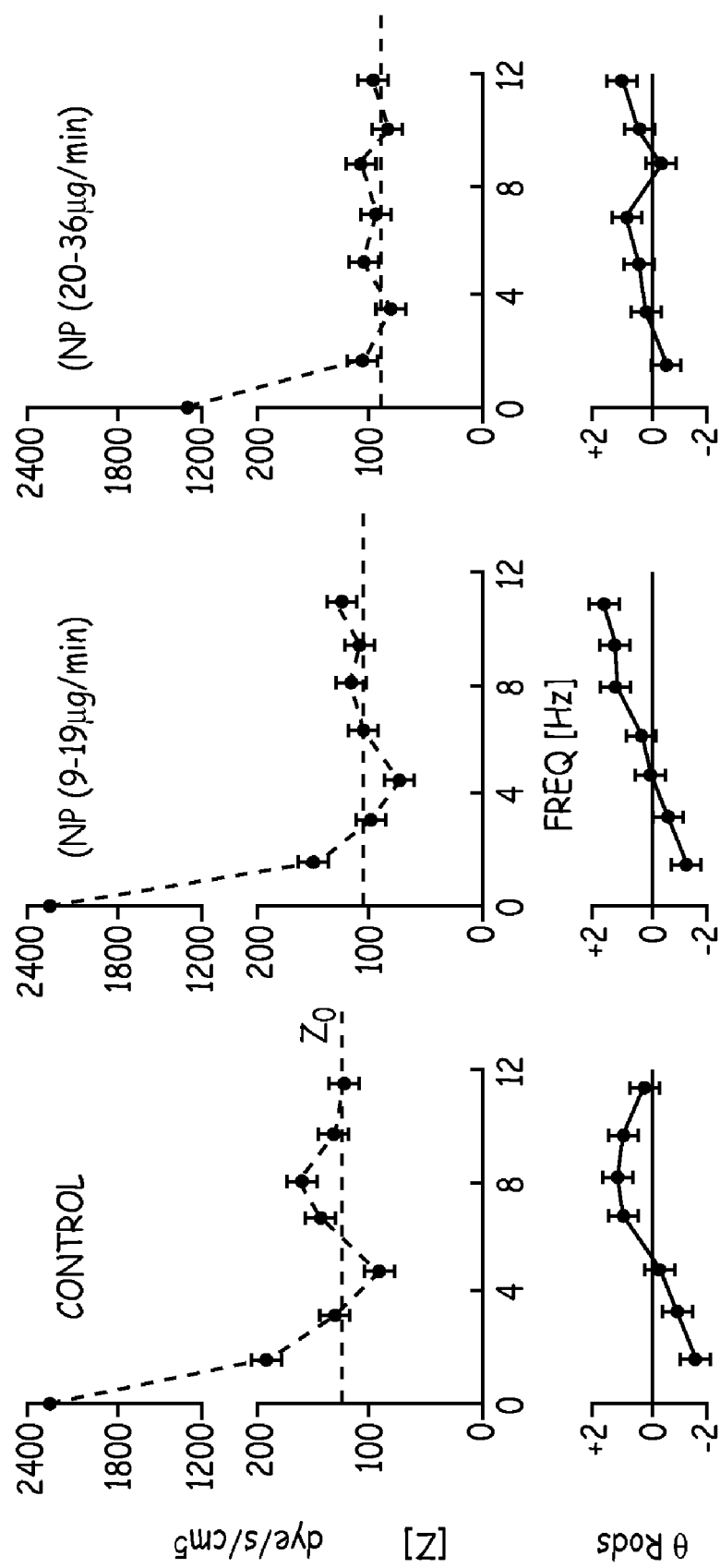
FIGS. 4(a)-(c) are plots of aortic impedance spectra, showing the frequency relationship between aortic pressures and flow, and the effect of drug therapy thereon.

The concept of LV afterload may be illustrated with reference to FIG. 4. FIG. 4 shows an aortic input impedance spectrum, formed by determining the frequency dependant relationship between aortic pressure and flow. The aortic input impedance spectrum has been proposed as a representation of LV afterload. Because of reflected waves in the arterial vasculature, the aortic input impedance spectrum may be characterized by the presence of local minima and maxima, as generally shown in FIG. 4. FIG. 4 shows the magnitude (top) and phase (bottom) composite aortic input impedance spectra from 12 patients during control (FIG. 4(a)) and during infusion of sodium nitroprusside (FIGS. 4(b) and (c)). Arterial vasodilation alters wave reflection patterns and peripheral resistance, and hence the location of local minima and maxima along the magnitude spectrum. Thus, pacing at a heart rate that corresponds to a local minimum of aortic impedance would tend to lower LV afterload and thereby improve cardiac efficiency and function. These local minima represent potential heart rates at which LV afterload may be lower than for other heart rates. Thus, it may be desirable to modulate heart rate so as to pace at a rate that minimizes LV afterload. Alternately, a feedback loop may be employed that uses the phasic component of LV afterload. For example, the device could adjust heart rate to a rate that corresponds to "zero" (or near zero) phasic component of aortic impedance, thereby minimizing the phasic component of LV afterload (or some other index of LV afterload), as described generally by Hettrick in U.S. Pat. App. Publication 2004/0167410.

It should be noted that an implantable device adapted to perform the methods described above may additionally or alternately include drug dispensing capabilities to accomplish the function of reducing the base HR below the intrinsic rate. For example, a certain embodiment may dispense a drug to reduce HR in response to a measured parameter.

Figure 5A:
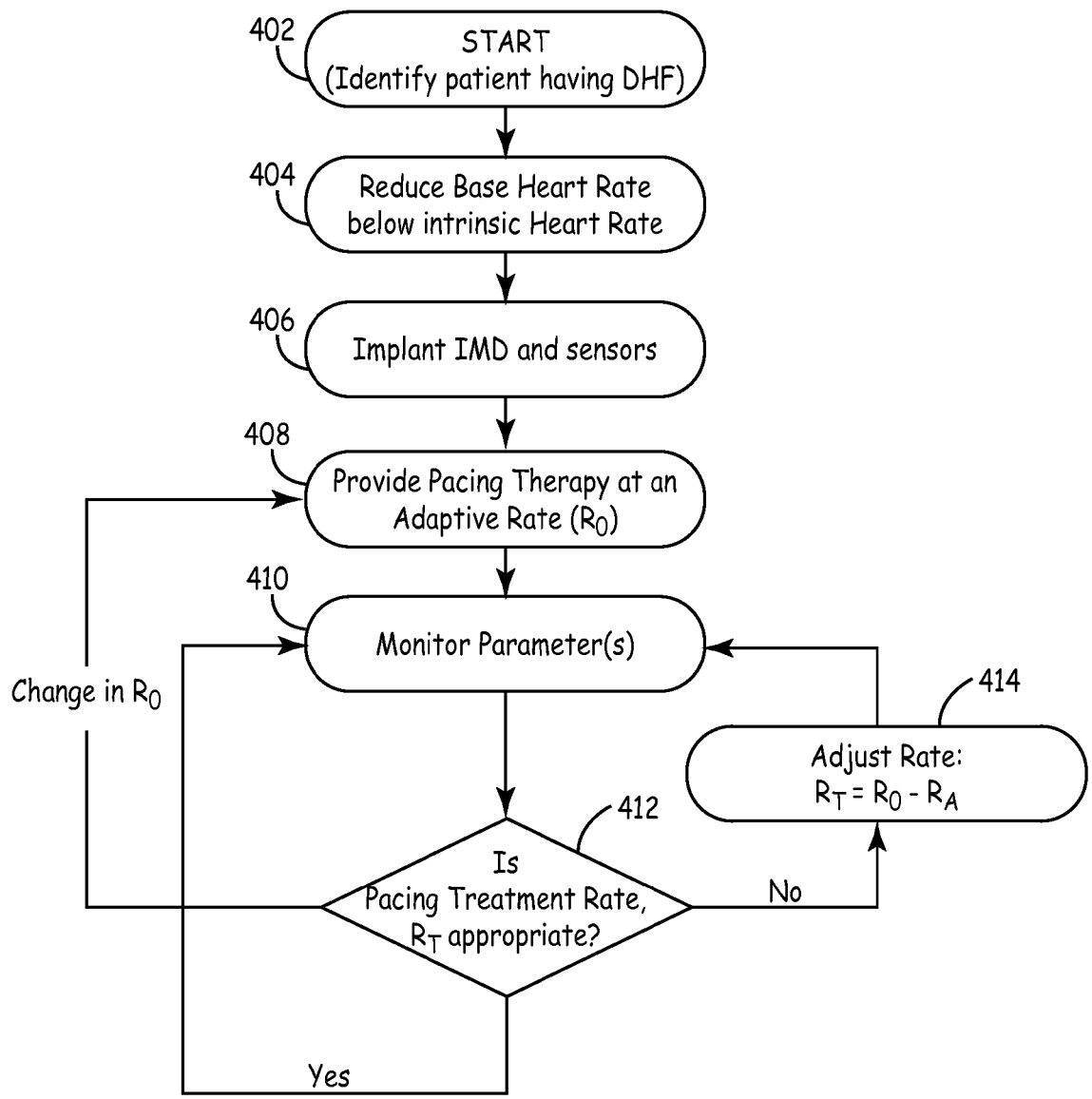
FIG. 5(a) is a flow diagram illustrating a method of treating a patient with DHF in accordance with an embodiment of the invention.

FIG. 5(a) is a flow diagram illustrating a method of treating diastolic heart failure (DHF) in accordance with an embodiment of the invention. Step 402 is the starting point, having previously identified a patient with DHF (e.g., having low cardiac output and associated symptoms, with a normal to elevated LV ejection fraction).

Step 404 comprises reducing a patient's "base heart rate" below the patient's "intrinsic heart rate." As used herein, the term "base heart rate" refers to the rate at which a patient's ventricles will mechanically contract with no intervention. For example, a normal heart in normal sinus rhythm may typically beat at a "base heart rate" of about 72 beats per minute (bpm). A patient's "intrinsic heart rate," as used herein, refers to the rate at which the sinoatrial (SA) node would control mechanical contractions of the heart chambers. Thus, in a normally functioning heart in normal sinus rhythm, the intrinsic heart rate and the base heart rate should be the same.

However, a patient's base heart rate may be altered by a number of different methods to thereby become different than the intrinsic heart rate. For example, an SA nodal ablation may be performed to remove the SA node, which may result in a lowered base heart rate that may range from about 30-50 bpm, since the ventricles will no longer contract at a rate controlled by the SA node. In this example, the intrinsic heart rate has not necessarily changed, since the SA node (if it were still present) would control the mechanical contractions of the heart chambers at a normal sinus rhythm rate greater than the lowered base HR. The intrinsic rate may also change due to exercise (e.g., an increase in intrinsic rate), or due to sleep (e.g., a decrease in intrinsic rate), for example.

Methods of causing a patient's base heart rate to decrease below an intrinsic rate may include the aforementioned SA nodal ablation, a procedure which is known to those of ordinary skill in the art. Other methods may include the administration of drug therapy, including bradycardic drugs such as beta-blockers and/or specific bradycardic agents (e.g., ULFS-49), for example, and the performance of an AV nodal ablation, as but two examples which would also be apparent to those having ordinary skill in the art. Causing a patient's base heart to decrease below an intrinsic rate using any of the above methods may cause the patient to rely on pacing therapy to control and/or modulate their heart rate at hemodynamically acceptable rates.

Certain embodiments of the invention may include implanting an implantable medical device (IMD) system and/or sensors in the patient, as indicated at Step 406 in FIG. 5(a). An IMD, such as a cardiac pacemaker or implantable cardioverter defibrillator, may be adapted to deliver cardiac pacing therapy, for example, and may further be adapted to receive signals related to physiologic information from the patient, which may be incorporated into therapy decisions made by the IMD, in certain embodiments. Sensors may provide information about a variety of physiological parameters, such as hemodynamic pressures, impedance, volumes, temperatures, activity, and postures, for example without limitation, as described herein.

In certain embodiments of the invention, cardiac pacing therapy may be delivered at an adaptive rate, $R_O$, as indicated at Step 408 in FIG. 5(a). Adaptive rate $R_O$ may be a rate determined by a number of rate-adaptive pacing schemes, as are known in the art. For example, an accelerometer or piezoelectric sensor may provide an adaptive rate based on forces or vibrations detected by the respective sensor. The adaptive rate may also be determined by a physiologic sensor, such as a minute ventilation sensor, which may use impedance measurements (e.g., transthoracic impedance) to monitor changes in respiration rate, for example, and to calculate an adaptive rate based therefrom, for example.

Adaptive rate $R_O$ may be adjusted or modulated in certain embodiments of the invention to improve cardiac efficiency or output as suggested by steps 410, 412, and 414 in FIG. 5(a). For example, adaptive rate $R_O$ may be determined in step 408 to be an exercise-induced rate that is higher than a patient's normal resting heart rate. However, the increase in HR to $R_O$ may not be appropriate for a patient with DHF for the reasons described above. In step 410, one or more parameters are monitored, and the results are used to determine whether the pacing treatment rate, $R_T$, is appropriate or optimal in step 412. If step 412 determines that the pacing treatment rate, $R_T$, is not optimal, the treatment rate $R_T$ may be adjusted in step 414 by applying an offset or adjustment, $R_A$, to the current treatment rate $R_T$:

$$R_T = R_O - R_A \tag{Eq. 1}$$

Steps 410, 412, and 414 may form a feedback loop that continually attempts to improve the cardiac efficiency or output by adjusting the treatment rate $R_T$. In many cases, the initial adjustment $R_A$ will result in a $R_T$ that is lower than the adaptive rate $R_O$, however, this is not necessary true (i.e, $R_A$ could be a positive or negative value in Eq. 1).

Step 410 may include monitoring one or more parameters such as hemodynamic pressures, oxygen saturation levels, sonomicrometry measurements, and impedance measurements, for example without limitation. Further, combinations of these signals and/or values derived from these signals may also be used in Step 412 to determine whether the pacing treatment rate $R_T$ is appropriate.

Step 412 may next evaluate one or more monitored patient parameters from step 410 and may determine whether the current treatment rate $R_T$ is appropriate for the particular patient. It should be noted that the adaptive rate $R_O$ may change (e.g., due to a change in exercise activity) and may require an update during the above-described process. In some embodiments, this update to $R_O$ may be performed while maintaining $R_A$ at its current value (rather than re-setting to zero) to avoid any sudden changes in $R_T$.

Steps 412 and 414 may include additional methods of evaluating the parameters monitored in step 410, both for determining the appropriateness of $R_T$, and for determining the adjustment $R_A$, as will be described in more detail with respect to FIGS. 8 and 9 below.

Figure 5B:
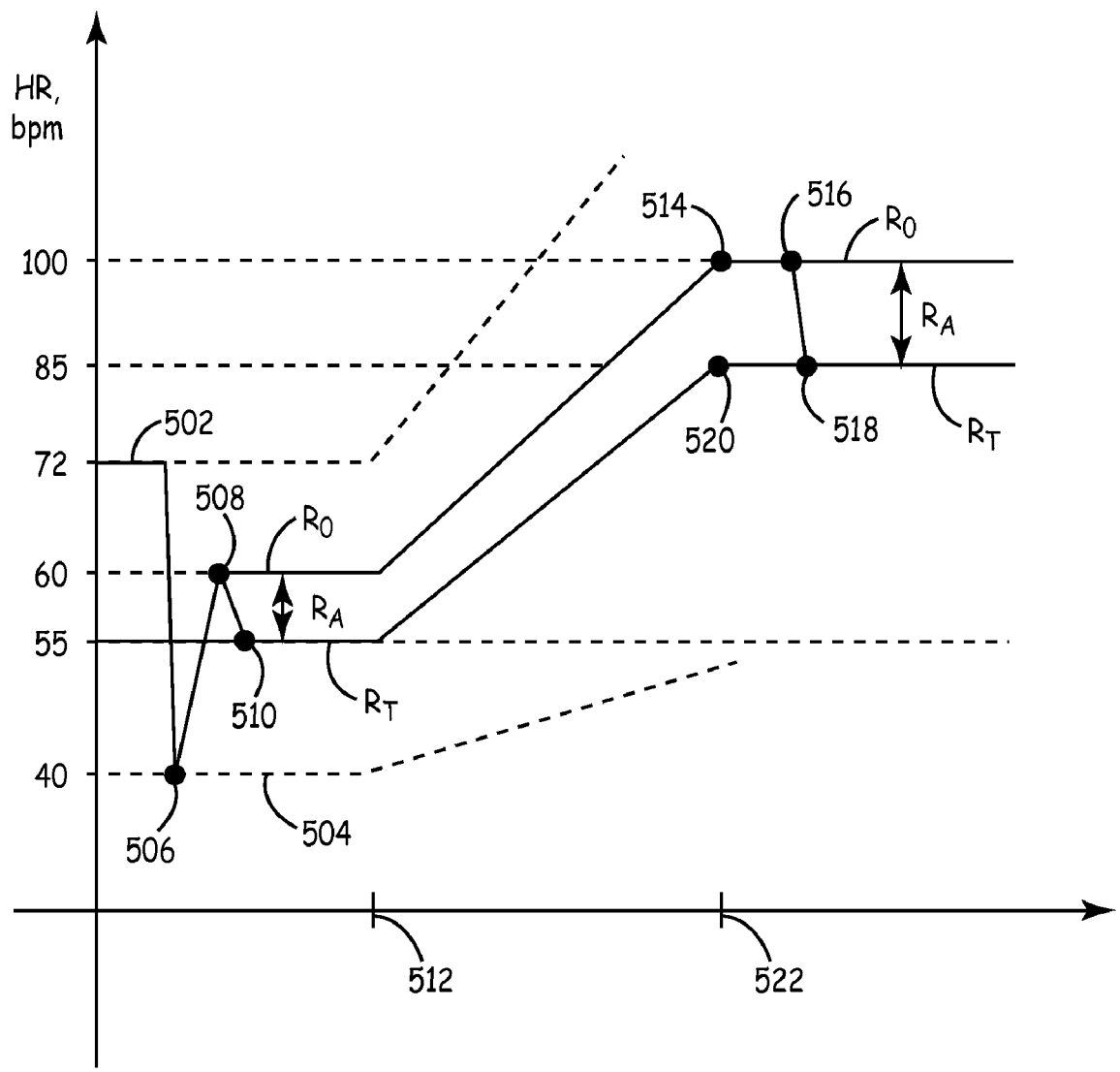
FIG. 5(b) is a conceptual plot of heart rate being modulated in a DHF patient according to certain embodiments of the invention.

FIG. 5(b) is a conceptual plot of heart rate (HR) over time for an exemplary DHF patient, illustrating an example of controlling HR according to various embodiments of the invention. Starting at the far left-hand side of the plot, the patient has an intrinsic heart rate 502, which equals the patient's base HR 504 of about 72 bpm (e.g., normal sinus rhythm, at rest). The patient's base HR 504 is then lowered below the intrinsic HR 502 to a rate of about 40 bpm as shown at point 506, for example, via SA nodal ablation or other techniques which may be available to those of ordinary skill in the art. Cardiac pacing therapy may then be delivered to the patient to provide a hemodynamically acceptable pacing treatment rate, $R_T$. For example, an implantable cardiac pacing system may be programmed to deliver rate-adaptive (or rate-responsive) pacing to increase the base HR to a pacing treatment rate, $R_T$, which may also correspond to an adaptive rate $R_O$ of about 60 bpm, as shown at point 508 (e.g., corresponding to the patient still being at rest). Next, the pacing treatment rate, $R_T$, may be adjusted according to certain embodiments of the invention by changing (i.e., increasing or decreasing) the adaptive rate $R_O$ by an adjustment or offset amount, $R_A$, resulting in the new pacing treatment rate, $R_T$, shown at point 510. For example, treatment rate $R_T = R_O - R_A = 60 - 5$ bpm=55 bpm (at rest) for the example shown in FIG. 5(b). The adjustment or offset amount, $R_A$, may be determined based upon evaluation of one or more measured or monitored patient parameters, generally as described above, and as described in more detail below.

In the example shown in FIG. 5(b), the patient begins some form of exercise (or other activity resulting in an increase in adaptive rate $R_O$), for example, at time 512. (The term "exercise" may include a variety of routine activities, such as walking up or down stairs, or even just getting up out of a chair, for example.) Adaptive rate $R_O$ is shown to increase from a value of about 60 bpm at time 512, to a value of about 100 bpm at time 514. In certain embodiments, the pacing treatment rate $R_T$ may track the adaptive rate $R_O$ for a period of time before being adjusted by $R_A$, for example, as shown at points 514, 516, and 518 in FIG. 5(b). In this example, the pacing treatment rate $R_T$ is adjusted after a certain period of time elapses after the commencement of exercise, corresponding to time 522 in FIG. 5(b). Here, $R_T = R_O - R_A = 100$ bpm−15 bpm=85 bpm, and the adjustment $R_A$ may be determined by evaluation of one or more monitored patient parameters. In certain other embodiments of the invention, the pacing treatment rate $R_T$ may be adjusted by an amount $R_A$ as shown at point 510 (e.g., from an earlier determination of $R_A$), and the adjustment may continue to be applied to $R_O$ throughout the transition from rest to exercise to provide an adjusted pacing treatment rate $R_T$ as shown at point 520 (e.g., the rate $R_T$ increases up to 85 bpm, rather than up to 100 bpm before being adjusted downward to 85 bpm in this example). Either of the above techniques may be used according to various embodiments of the invention to determine and provide a treatment rate $R_T$, as well as other techniques that may become apparent to one of ordinary skill in the art with the benefit of these teachings.

Figure 6:
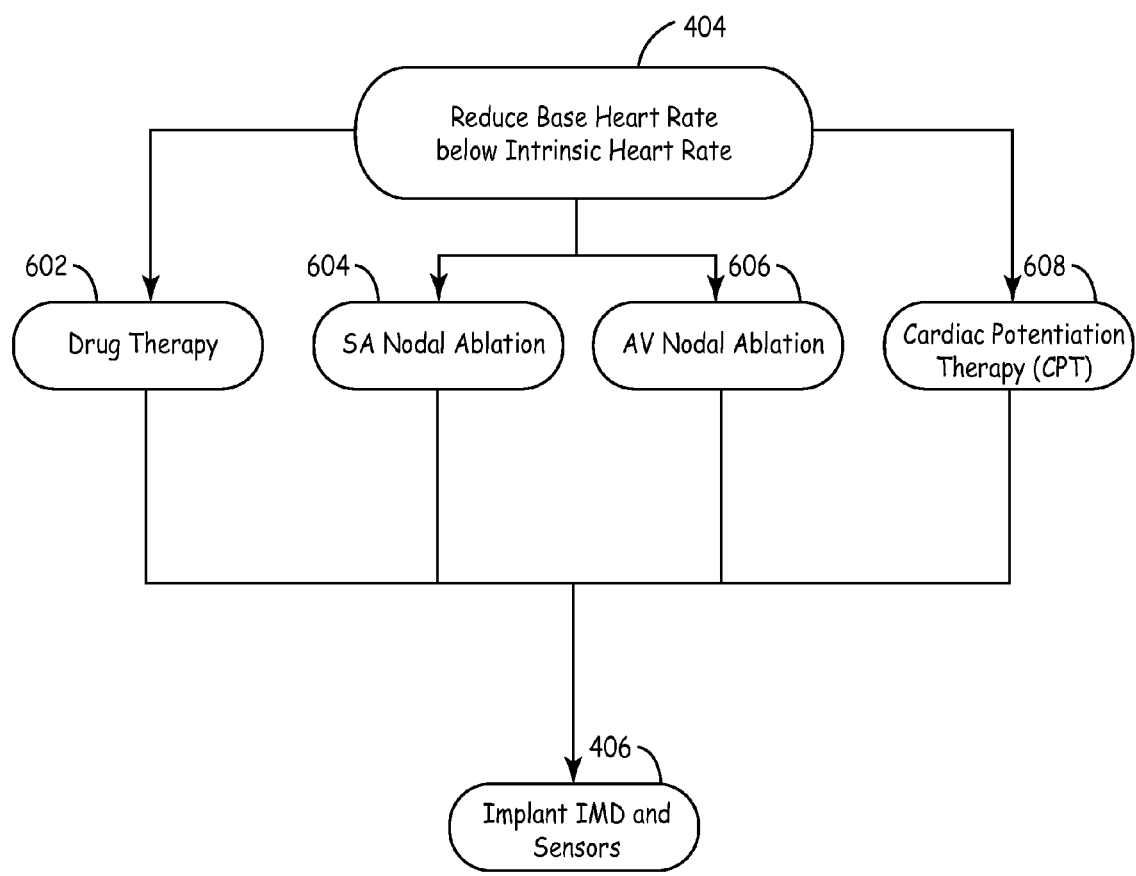
FIG. 6 is a flow diagram illustrating alternate methods of reducing a patient's base heart rate for the method described in FIG. 5(a)

FIG. 6 shows examples of ways to slow the patient's heart rate below its intrinsic rate according to Step 404 in FIG. 5(a). For example, drug therapy 602 may be used to lower a patient's base HR, as described above. Other methods may include ablation of the sino-atrial (SA) node 604, and ablation of the atrio-ventricular (AV) node 606. Cardiac potentiation therapy (CPT) 608 may also be used to slow a patient's base HR according to certain embodiments of the invention. CPT is a pacing therapy that employs post extra-systolic potentiation (PESP). The PESP effect may be created via the delivery of properly timed coupled or paired pacing stimuli, for example, and may be used to lengthen the cardiac cycle, which may effectively lower a patient's base HR.

Figure 7:
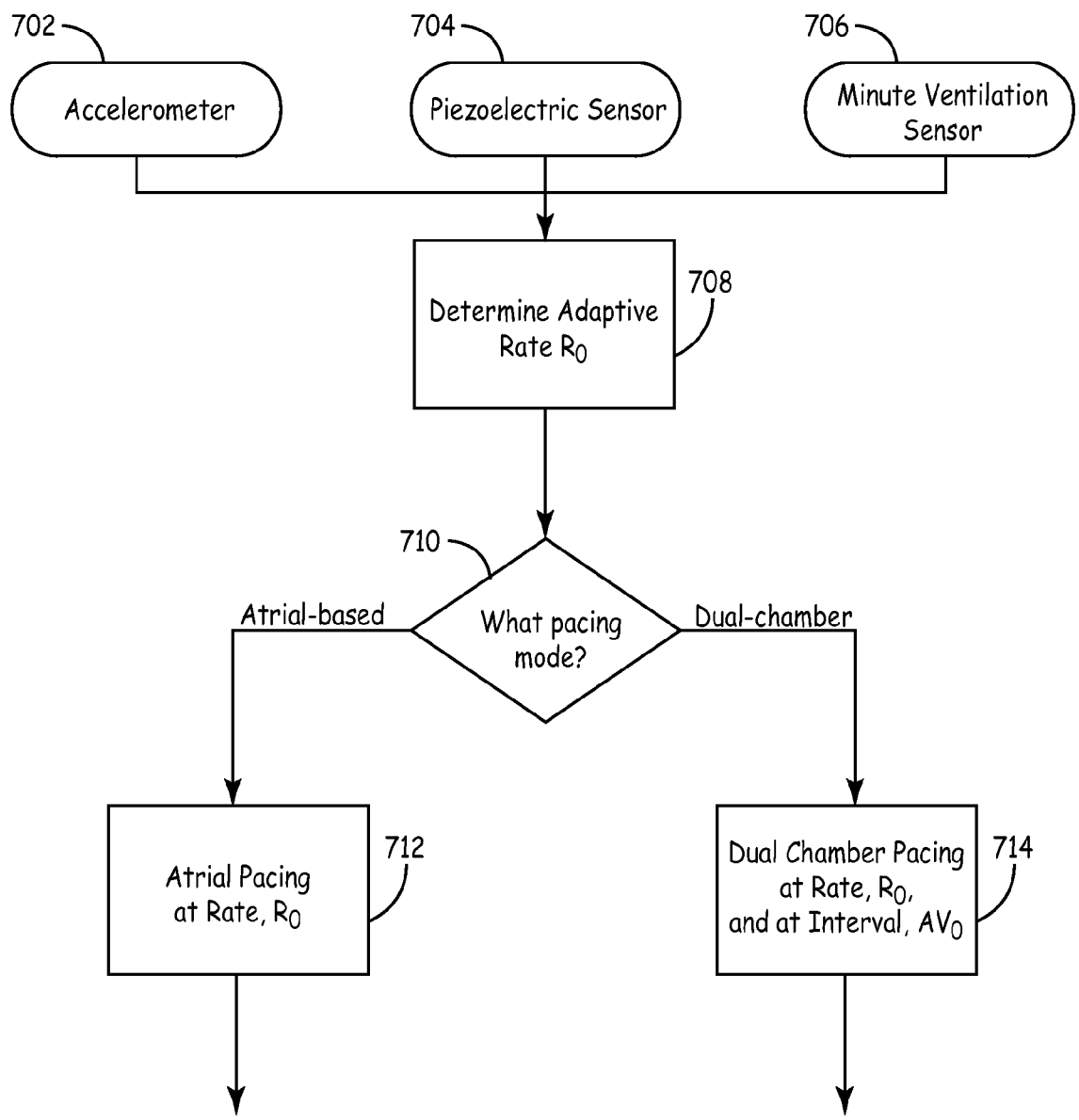
FIG. 7 is a flow diagram illustrating a method of determining a patient's adaptive rate, $R_0$.

FIG. 7 illustrates several exemplary ways of controlling heart rate using pacemaker therapy according to Step 408 (from FIG. 5(a)). Rate-responsive or rate-adaptive pacing techniques as are known in the art may be used to increase heart rate above a programmed rate (e.g., above a lower rate limit), typically in response to exercise or other activity of the patient. For example, a sensor, such as an accelerometer sensor 702, a piezoelectric sensor 704, or a minute ventilation sensor (e.g., a transthoracic impedance sensor) 706, or any combination of the above sensors, may be used to provide rate-adaptive pacing at an adaptive rate, $R_O$, above the programmed lower rate limit, as shown in step 708. In certain embodiments of the invention, a pacing mode may be selected at step 710, which selection may be based in part on the method used to reduce the patient's base HR in step 404 (FIG. 5(a)). Atrial pacing 712 in the AAI or AAIR modes at a rate $R_O$ may be employed in certain preferred embodiments, which may allow intrinsic conduction through the AV node and into the ventricles, which may further provide improved cardiac output. Alternately, certain dual-chamber pacing modes 714 may be employed at a rate $R_O$ according to other preferred embodiments of the invention. Dual-chamber pacing 714 may include the determination of a rate-adaptive AV interval (or AV pacing delay), which may allow for additional control over ventricular filling time in certain embodiments of the invention.

Of course, a variety of pacing schemes are known to those of ordinary skill in the art, many of which may be used with embodiments of the invention. Such use is contemplated and would be considered to fall within the scope of the invention as claimed herein.

Figure 8:
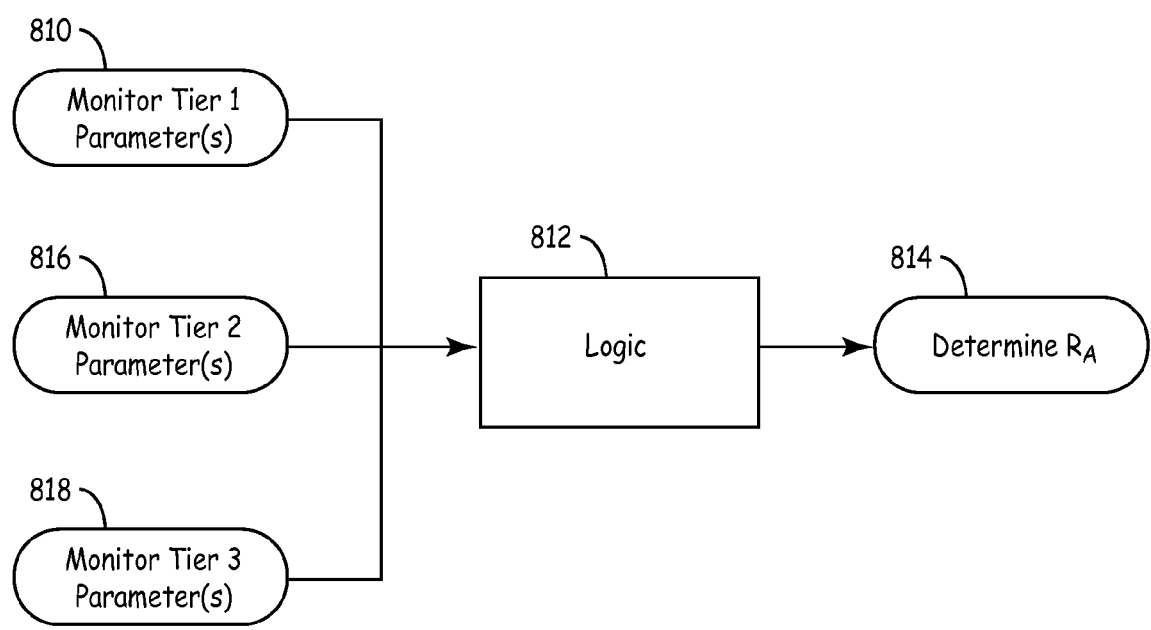
FIG. 8 is a flow diagram that illustrates a method of adjusting a patient's adaptive rate based on monitored patient parameters in accordance with an embodiment of the invention.

FIG. 8 illustrates an example of the use of a plurality of monitored patient parameters that may be used to provide information/feedback to adjust a pacing parameter according to embodiments of the invention. The example illustrated in FIG. 8 is analogous to steps 410, 412, and 414 described with respect to FIG. 5(a) above. The plurality of monitored patient parameters may be categorized according to the speed at which the measured parameter may become available (e.g., the speed at which changes in the parameter may be observable). For example, a "first tier" of parameters 810 may include signals that may be obtained (or may change, or may be updated) relatively frequently (e.g., roughly every 5-10 seconds). Such first tier signals 810 may include hemodynamic pressure signals measured using pressure sensors mounted on a transvenous pacing lead, for example without limitation. Such hemodynamic pressure signals may include right ventricular pressure (RVP), left ventricular pressure (LVP), the slope of RVP or LVP (e.g., dP/dt), and estimated pulmonary arterial diastolic (ePAD) pressure (which may be derived from other parameters, such as RVP and LVP), by way of example without limitation. Other examples of first tier parameters 810 that may be monitored and/or measured include a deceleration signal (i.e., a decrease in acceleration) measured at the LV wall in response to LV wall motion, as well as accelerometer and/or sonomicrometry signals, which may be used, for example, to provide measurements of acceleration for this purpose.

A "second tier" of parameters 816 may include signals that may be obtained (or may change, or may be updated) somewhat less frequently than the first tier parameters 810 (e.g., roughly every 10-60 seconds). Such second tier signals or parameters 816 may include hemodynamic parameters indicative of oxygen content in the blood, such as coronary venous oxygen saturation. Central or mixed venous oxygen saturation ($SCVO_2$ or $SVO_2$) are examples of second tier parameters 816 that may be measured or derived from signals obtained using a light-based sensor placed in the pulmonary outflow tract, for example without limitation.

A "third tier" of parameters 818 may include signals that may be obtained (or may change, or may be updated) relatively infrequently (e.g., roughly every 1-10 minutes). Such third tier signals or parameters 818 may include relatively slowly changing signals such as transthoracic impedance, minute ventilation signals, and LV afterload, or signals representative thereof (e.g., $Z_a$, to be described in more detail below).

The use of multiple tiers (e.g., two or more tiers) of monitored patient parameters may allow for further refinement of the pacing parameters provided in accordance with embodiments of the invention, including refinement of the rate adjustment, $R_A$. At step 812, for example, logic functions may be applied to input monitored patient parameters 810, 816, and 818 as they are received. In one possible embodiment, logic functions may be applied to the various tiers of monitored patient parameters, for example, to provide a weighted sum of the input values. The weighted sum may, for example, be compared to a predetermined threshold value and, if the weighted sum is above the predetermined threshold, may cause an action to be taken (e.g., to perform a re-calculation of the rate adjustment, $R_A$). Alternately or additionally, a weighted sum as described above may be used to determine the magnitude of the action taken (e.g., to calculate the amount of the rate adjustment, $R_A$). This step may be considered a separate step, as shown at step 814 in FIG. 8, or may be incorporated in the logic of step 812, for example. Certain embodiments may include the ability to determine $R_A$ as a function of the adaptive rate, $R_0$, for example, as part of the logic of step 812. The adaptive rate, $R_0$, may be used either alone or in conjunction with the monitored patient parameters in the logic of step 812 to determine the rate adjustment $R_A$ according to certain embodiments of the invention.

In an alternate embodiment of the logic step 812, a tier (or tiers) of monitored patient parameters may be used to confirm an action taken based upon another tier (or tiers) of monitored patient parameters. For example, a rate change or rate adjustment $R_A$ based on a $1^{st}$ tier signal 810 may be confirmed if either the $2^{nd}$ or $3^{rd}$ tier signals 816, 818 (or both) include a strong confirmation signal (i.e., the monitored patient parameters of the $2^{nd}$ and $3^{rd}$ tier indicate that the action taken in response to the $1^{st}$ tier signal 810 was appropriate). This may occur, for example, if a $1^{st}$ tier parameter such as RVP increases, and $R_A$ is adjusted to provide a lower treatment rate $R_T$. A subsequent increase in coronary venous oxygen saturation (e.g., a $2^{nd}$ tier parameter) and/or an increase in transthoracic impedance (e.g., a $3^{rd}$ tier parameter) indicating less pulmonary congestion may confirm that the rate adjustment was appropriate, and may suggest additional adjustment in the same direction. Conversely, if the $2^{nd}$ and/or $3^{rd}$ tier signals contradict the information and decision based on the $1^{st}$ tier signal, this information may be used in the logic of step 812 to alter the action taken based on the $1^{st}$ tier signal, according to certain embodiments of the invention. For example, contradictory information from the $2^{nd}$ and/or $3^{rd}$ tier signals may cause the action taken based upon the $1^{st}$ tier signal (e.g., an increase in $R_A$, resulting in a lower $R_T$) to be cancelled, or modified, or lessened to a certain extent (e.g., a smaller increase in $R_A$) in some embodiments.

The adjustments to HR described above may be performed on a substantially continuous basis, for example, to continually adjust the pacing rate on an on-going basis, according to the methods described above. Alternately, certain embodiments of the invention may employ an intermittent or acute technique that "detects" a condition (e.g., according to a detection algorithm), and performs an adjustment to pacing parameters that may last only while the condition persists (e.g., according to an algorithm). This may, for example, be part of steps 410 and 412 in FIG. 5(*a*). In some embodiments, an intermittent "detection" algorithm may comprise calculating an adaptive rate $R_0$ and a rate adjustment $R_A$ on an ongoing basis, but only applying the rate adjustment to calculate a new treatment rate ($R_T = R_0 - R_A$) if a certain setpoint or threshold is reached. An example of such a setpoint may include predetermined values of $R_0$, $R_A$, and/or $R_T$ that, if exceeded, will trigger the actual adjustment in rate. Thus, $R_T$ may equal $R_0$ until $R_0$ goes above a certain rate (e.g., 80 bpm), at which point the rate adjustment $R_A$ may be calculated (if not already done) and applied to $R_0$ to yield a new treatment rate, $R_T$. As a further illustration, the adjustment to rate may continue to be applied, for example, until $R_0$ decreases below some predetermined setting (e.g., 75 bpm) to end the episode and/or terminate the intermittent therapy, according to certain embodiments of the invention.

As noted above, a detection algorithm may simply detect the presence of an adaptive rate $R_0$ that is more than a certain threshold rate, in certain embodiments. In other possible embodiments, a detection algorithm may detect the presence of an adaptive rate that changes more than a certain amount within a certain time period, for example. In still further embodiments, a weighted average (or other logical function) of the tiers of parameters may form the basis for a detection algorithm. These and other such modifications are contemplated and would be deemed to fall within the scope of the invention as claimed.

Figure 9:
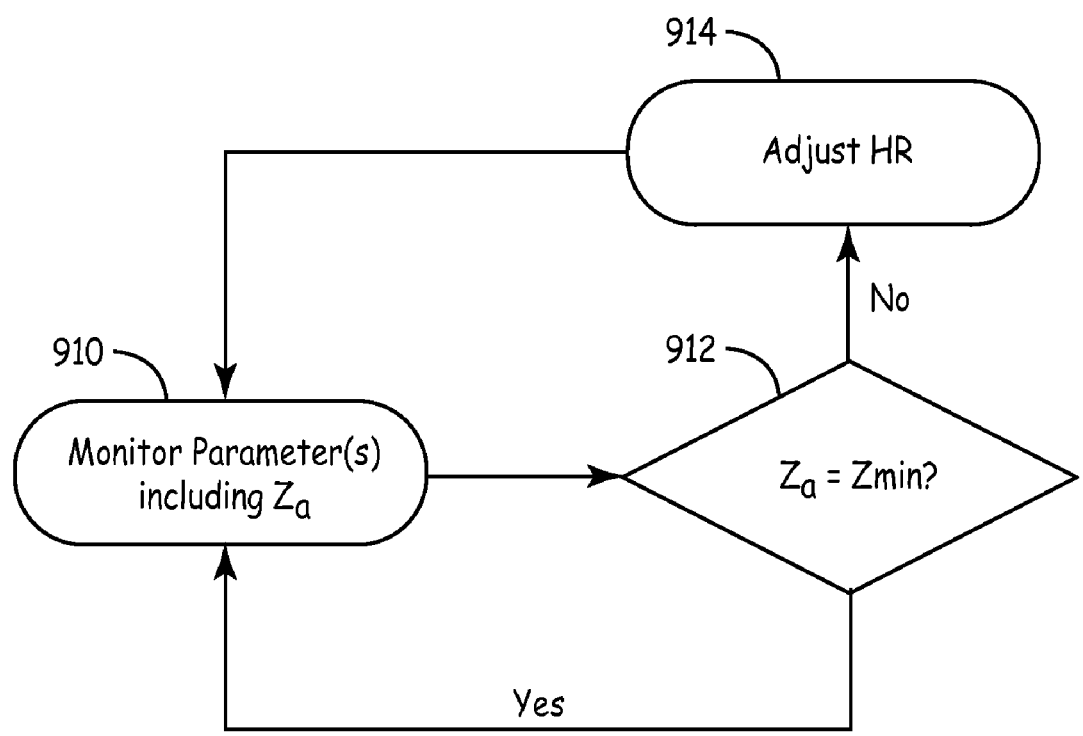
FIG. 9 is a flow diagram illustrating a method of adjusting a patient's adaptive rate based on measured aortic impedance in accordance with embodiments of the invention.

FIG. 9 is a flow diagram of a method of treating a DHF patient that includes adjusting heart rate based on a measured aortic impedance parameter, $Z_a$. As shown in FIG. 9, an alternate embodiment of the invention may include a feedback loop that attempts to minimize $Z_{min}$ by adjusting HR. FIG. 9 shows steps 910, 912, and 914, which correspond to steps 410, 412, and 414 in the method illustrated in FIG. 5(*a*). However, step 912 in FIG. 9 simply seeks to minimize the value of measured aortic impedance, $Z_a$, by adjusting HR to find a minimum value of aortic impedance ($Z_{min}$). As previously noted, aortic impedance $Z_a$ may be measured and/or estimated from measured aortic pressures and/or flow.

Thus, embodiments of the METHOD AND APPARATUS FOR TREATING DIASTOLIC HEART FAILURE are disclosed. One skilled in the art will appreciate that the invention can be practiced with embodiments other than those disclosed. The disclosed embodiments are presented for purposes of illustration and not limitation, and the invention is limited only by the claims that follow.

The invention claimed is:

1. A method of treating a patient responsive to a diagnosis of diastolic heart failure (DHF), the method comprising:
   causing the patient's heart rate to decrease below the patient's intrinsic heart rate;
   sensing the patient's level of exercise and level of left ventricular afterload;
   determining an adaptive heart rate $R_O$ as a function of the patients level of exercise;
   determining a rate adjustment $R_A$ as a function of the patient's level of ventricular afterload;
   adjusting the adaptive rate, $R_O$, by the rate adjustment, $R_A$, to provide exercise responsive pacing at a treatment rate, $R_T$, corresponding to a desired level of left ventricular afterload;
   and delivering cardiac pacing therapy to the patient at the treatment rate.

2. The method of claim 1 wherein determining the rate adjustment, $R_A$, comprises determining the rate adjustment as a function of aortic impedance.

3. The method of claim 1 wherein determining the adaptive rate, $R_O$, comprises deriving the adaptive rate from an activity sensor.

4. The method of claim 1 wherein determining the adaptive rate, $R_O$, comprises deriving the adaptive rate from a physiologic sensor.

5. The method of claim 1 wherein $R_A$ is a function of $R_O$.

6. The method of claim 1 comprising triggering application of the rate adjustment, $R_A$, when the patient's level of left ventricular afterload crosses a predetermined threshold.

7. The method of claim 1 wherein determining $R_T$ comprises subtracting $R_A$ from $R_O$.

* * * * *